United States Patent [19]

Bredt et al.

[11] Patent Number: 5,268,465
[45] Date of Patent: Dec. 7, 1993

[54] PURIFICATION AND MOLECULAR CLONING OF NITRIC OXIDE SYNTHASE

[75] Inventors: David S. Bredt; Solomon H. Snyder, both of Baltimore, Md.

[73] Assignee: The Johns Hopkins University, Baltimore, Md.

[21] Appl. No.: 642,002

[22] Filed: Jan. 18, 1991

[51] Int. Cl.$^5$ ............................................. C12N 15/00
[52] U.S. Cl. .............................. 435/252.3; 435/69.1; 935/14; 536/23.2
[58] Field of Search ......................... 536/27; 435/69.1

[56] References Cited

PUBLICATIONS

Deryak, R., et al., 1984, Cell 38:287-297.
Bredt, D. S., et al., 1990, Society for Neuroscience Abstracts, 16(2): [20th Annual Meeting of the Society for Neuroscience] p. 967, No. 400.10.
Moyer, B., et al., 1990, FEBS Letters, 277(1,2): 215-219.
Knowles, R. G., et al., 1990, in *Nitric Oxide from L-Arginine: A Bioregulatory System*, Moncada, S., et al. Eds., pp. 139-146.
Knowles, R. G., et al., 1990, Biochemical Journal 269:207-210.
Knowles, R. G., et al. 1990, Biochemical Journal 270: 833-836.
Murphy, M., 1990, Biochemical Journal 271: 563-564.
Hewick, R. M., et al., 1981, The Journal of Biological Chemistry 256(15): 7990-7997.
Lathe, R., 1985, Journal of Molecular Biology 183:1-12.
Frohman, M. A., et al., 1988, Proceedings, National Academy of Sciences, USA 85: 8998-9002.
Kosuga, K., et al., 1990, Biochemical and Biophysical Research Communications, 172 (2): 705-708.
Palacios, M., et al., 1989, Biochemical and Biophysical Research Communications 165(2):802-809.
Rees, D. D., et al., 1990, Biochemical and Biophysical Research Communications, 173(2):541-547.
Kwon, N. S., Nathan, C. F. & Stuehr, D. J., (1989) The Journal of Biological Chemistry, 264:20496-20501.
Furchgott, R. F. & Vanhoutte, P. M. (1988) FASEB J. 3:2007-2018.
Tayeh, M. A. & Marletta, M. A., (1989) The Journal of Biological Chemistry 264:19654-19658.
Bredt, D. S., Hwang, P. M. & Snyder, S. H., (1990) Nature, 347:768-770.
Bredt, D. S., & Snyder, S. H., (1990) Proc. Natl. Acad. Sci. USA, 87:682-685.
Bredt, D. S., & Snyder, S. H., (1989) Proc. Natl. Acad. Sci. USA, 86:9030-9033.
Ignarro, L. J., (1990) Annu Rev. Pharmacol. Toxicol., 30:535-560.

*Primary Examiner*—Robert A. Wax
*Assistant Examiner*—William W. Moore
*Attorney, Agent, or Firm*—Banner, Birch, McKie & Beckett

[57] ABSTRACT

A method of purifying calmodulin-dependent nitric oxide synthase provides a homogeneous preparation of the enzyme. The enzyme is used to raise antibodies which are a useful immunohistochemical reagent. The antibodies localize calmodulin-dependent nitric oxide synthase to a number of anatomical sites, including retina, intestine, adrenal gland, and vasculature. However, activated macrophages, which are known to possess a nitric oxide producing activity, do not display an immunoreactive protein of appropriate size on Western blots using the antibodies. Nucleotide sequences encoding calmodulin-dependent nitric oxide synthase indicate a novel sequence with a flavin binding site consensus sequence.

11 Claims, 3 Drawing Sheets

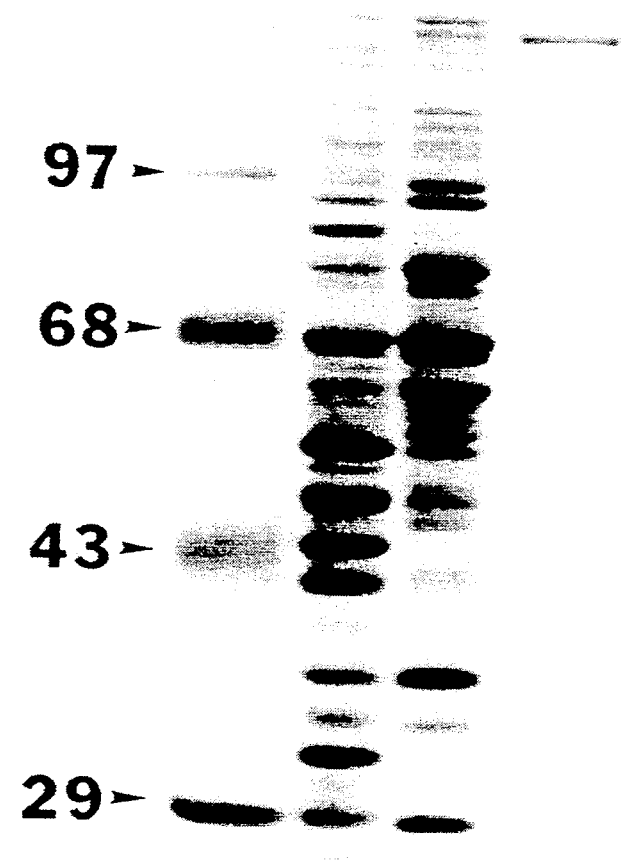

5,268,465

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5108 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: N ( i v ) ANTI-SENSE: N ( v i ) ORIGINAL SOURCE:
        ( A ) ORGANISM: Rattus rattus
        ( F ) TISSUE TYPE: Brain ( i x ) FEATURE:
    ( A ) NAME/KEY: CDS
    ( B ) LOCATION: 400..4686
    ( D ) OTHER INFORMATION:

( x i ) SEQUENCE DESCRIPTION: SEQ ID NO:1:

```
CTTTTTTTTT TTTTTTTTT TTTTTTTTT TTTTATATAA ATAAAAACCT CACGTCTGAC    60

AAGCTGGTGA CCAAGATGCC CAGAGACTAG ACCCTATGCT TGTGAGTCAC AGTCATCAGA   120

CACGGCAAAC CTCCAGTCTT CCTGACCTGT TGCTTAGGGA CACATCCGT  TGCTGCCCCT   180

GACGTCTGCC TGGTCAACCT TGACTTCCTT TGAGAGTAAG GAAGGGGGCG GGGACACGTT   240

GAAATCATGC CACCCAAGGC CGAATCGGAA TGAGCAGATG ACGCCAAGTT GACGTCAAAG   300

ACAGAGGCGA CAGAAACTCT GCAGCCAGCT CTTGCCCCCG AGGAGCTCAG GTTCCTGCAG   360

GAGTCATTTT AGCTTAGTCT TCTGAAGGAC ACAGATACC ATG GAA GAG AAC ACG     414
                                           Met Glu Glu Asn Thr
                                           1               5

TTT GGG GTT CAG CAG ATC CAA CCC AAT GTA ATT TCT GTT CGT CTC TTC    462
Phe Gly Val Gln Gln Ile Gln Pro Asn Val Ile Ser Val Arg Leu Phe
         10                  15                  20

AAA CGC AAA GTG GGA GGT CTG GGC TTC CTG GTG AAG GAA CGG GTC AGC    510
Lys Arg Lys Val Gly Gly Leu Gly Phe Leu Val Lys Glu Arg Val Ser
             25                  30                  35

AAG CCT CCC GTG ATC ATC TCA GAC CTG ATT CGA GGA GGT GCT GCG GAG    558
Lys Pro Pro Val Ile Ile Ser Asp Leu Ile Arg Gly Gly Ala Ala Glu
         40                  45                  50

CAG AGC GGC CTT ATC CAA GCT GGA GAC ATC ATT CTC GCA GTC AAC GAT    606
Gln Ser Gly Leu Ile Gln Ala Gly Asp Ile Ile Leu Ala Val Asn Asp
     55                  60                  65

CGG CCC TTG GTA GAC CTC AGC TAT GAC AGT GCC CTG GAG GTT CTC AGG    654
Arg Pro Leu Val Asp Leu Ser Tyr Asp Ser Ala Leu Glu Val Leu Arg
 70                  75                  80                  85

GGC ATT GCC TCT GAG ACC CAC GTG GTC CTC ATT CTG AGG GGC CCT GAG    702
Gly Ile Ala Ser Glu Thr His Val Val Leu Ile Leu Arg Gly Pro Glu
             90                  95                  100

GGC TTC ACT ACA CAT CTG GAG ACC ACC TTC ACA GGG GAT GGA ACC CCC    750
Gly Phe Thr Thr His Leu Glu Thr Thr Phe Thr Gly Asp Gly Thr Pro
         105                 110                 115

AAG ACC ATC CGG GTG ACC CAG CCC CTC GGT CCT CCC ACC AAA GCC GTC    798
Lys Thr Ile Arg Val Thr Gln Pro Leu Gly Pro Pro Thr Lys Ala Val
         120                 125                 130

GAT CTG TCT CAC CAG CCT TCA GCC AGC AAA GAC CAG TCA TTA GCA GTA    846
Asp Leu Ser His Gln Pro Ser Ala Ser Lys Asp Gln Ser Leu Ala Val
     135                 140                 145

GAC AGA GTC ACA GGT CTG GGT AAT GGC CCT CAG CAT GCC CAA GGC CAT    894
Asp Arg Val Thr Gly Leu Gly Asn Gly Pro Gln His Ala Gln Gly His
 150                 155                 160                 165

GGG CAG GGA GCT GGC TCA GTC TCC CAA GCT AAT GGT GTG GCC ATT GAC    942
Gly Gln Gly Ala Gly Ser Val Ser Gln Ala Asn Gly Val Ala Ile Asp
             170                 175                 180

CCC ACG ATG AAA AGC ACC AAG GCC AAC CTC CAG GAC ATC GGG GAA CAT    990
Pro Thr Met Lys Ser Thr Lys Ala Asn Leu Gln Asp Ile Gly Glu His
             185                 190                 195

GAT GAA CTG CTC AAA GAG ATA GAA CCT GTG CTG AGC ATC CTC AAC AGT   1038
Asp Glu Leu Leu Lys Glu Ile Glu Pro Val Leu Ser Ile Leu Asn Ser
         200                 205                 210

GGG AGC AAA GCC ACC AAC AGA GGG GGA CCA GCC AAA GCA GAG ATG AAA   1086
Gly Ser Lys Ala Thr Asn Arg Gly Gly Pro Ala Lys Ala Glu Met Lys
     215                 220                 225

GAC ACA GGA ATC CAG GTG GAC AGA GAC CTC GAT GGC AAA TCG CAC AAA   1134
Asp Thr Gly Ile Gln Val Asp Arg Asp Leu Asp Gly Lys Ser His Lys
```

```
                230                        235                        240                        245
GCT  CCG  CCC  CTG  GGC  GGG  GAC  AAT  GAC  CGC  GTC  TTC  AAT  GAC  CTG  TGG           1182
Ala  Pro  Pro  Leu  Gly  Gly  Asp  Asn  Asp  Arg  Val  Phe  Asn  Asp  Leu  Trp
                    250                        255                        260

GGG  AAG  GAC  AAC  GTT  CCT  GTG  ATC  CTT  AAC  AAC  CCG  TAT  TCA  GAG  AAG           1230
Gly  Lys  Asp  Asn  Val  Pro  Val  Ile  Leu  Asn  Asn  Pro  Tyr  Ser  Glu  Lys
               265                        270                        275

GAA  CAG  TCC  CCT  ACC  TCG  GGG  AAA  CAG  TCT  CCC  ACC  AAG  AAC  GGC  AGC           1278
Glu  Gln  Ser  Pro  Thr  Ser  Gly  Lys  Gln  Ser  Pro  Thr  Lys  Asn  Gly  Ser
          280                        285                        290

CCT  TCC  AGG  TGC  CCC  CGT  TTC  CTC  AAG  GTC  AAG  AAC  TGG  GAG  ACG  GAC           1326
Pro  Ser  Arg  Cys  Pro  Arg  Phe  Leu  Lys  Val  Lys  Asn  Trp  Glu  Thr  Asp
     295                        300                        305

GTG  GTC  CTC  ACC  GAC  ACC  CTG  CAC  CTG  AAG  AGC  ACA  CTG  GAA  ACG  GGG           1374
Val  Val  Leu  Thr  Asp  Thr  Leu  His  Leu  Lys  Ser  Thr  Leu  Glu  Thr  Gly
310                        315                        320                        325

TGC  ACA  GAG  CAC  ATT  TGC  ATG  GGC  TCG  ATC  ATG  CTG  CCT  TCC  CAG  CAC           1422
Cys  Thr  Glu  His  Ile  Cys  Met  Gly  Ser  Ile  Met  Leu  Pro  Ser  Gln  His
                    330                        335                        340

ACG  CGG  AAG  CCA  GAA  GAT  GTC  CGC  ACA  AAG  GAC  CAG  CTC  TTC  CCT  CTA           1470
Thr  Arg  Lys  Pro  Glu  Asp  Val  Arg  Thr  Lys  Asp  Gln  Leu  Phe  Pro  Leu
               345                        350                        355

GCC  AAA  GAA  TTT  CTC  GAC  CAA  TAC  TAC  TCA  TCC  ATT  AAG  AGA  TTT  GGC           1518
Ala  Lys  Glu  Phe  Leu  Asp  Gln  Tyr  Tyr  Ser  Ser  Ile  Lys  Arg  Phe  Gly
          360                        365                        370

TCC  AAG  GCC  CAC  ATG  GAC  AGG  CTG  GAG  GAG  GTG  AAC  AAG  GAG  ATT  GAA           1566
Ser  Lys  Ala  His  Met  Asp  Arg  Leu  Glu  Glu  Val  Asn  Lys  Glu  Ile  Glu
     375                        380                        385

AGC  ACC  AGC  ACC  TAC  CAG  CTC  AAG  GAC  ACC  GAG  CTC  ATC  TAT  GGC  GCC           1614
Ser  Thr  Ser  Thr  Tyr  Gln  Leu  Lys  Asp  Thr  Glu  Leu  Ile  Tyr  Gly  Ala
390                        395                        400                        405

AAG  CAT  GCC  TGG  CGG  AAC  GCC  TCT  CGA  TGT  GTG  GGC  AGG  ATC  CAG  TGG           1662
Lys  His  Ala  Trp  Arg  Asn  Ala  Ser  Arg  Cys  Val  Gly  Arg  Ile  Gln  Trp
                    410                        415                        420

TCC  AAG  CTG  CAG  GTG  TTC  GAT  GCC  CGA  GAC  TGC  ACC  ACA  GCC  CAC  GGC           1710
Ser  Lys  Leu  Gln  Val  Phe  Asp  Ala  Arg  Asp  Cys  Thr  Thr  Ala  His  Gly
               425                        430                        435

ATG  TTC  AAC  TAC  ATC  TGT  AAC  CAT  GTC  AAG  TAT  GCC  ACC  AAC  AAA  GGG           1758
Met  Phe  Asn  Tyr  Ile  Cys  Asn  His  Val  Lys  Tyr  Ala  Thr  Asn  Lys  Gly
          440                        445                        450

AAT  CTC  AGG  TCG  GCC  ATC  ACG  ATA  TTC  CCT  CAG  AGG  ACT  GAC  GGC  AAA           1806
Asn  Leu  Arg  Ser  Ala  Ile  Thr  Ile  Phe  Pro  Gln  Arg  Thr  Asp  Gly  Lys
     455                        460                        465

CAT  GAC  TTC  CGA  GTG  TGG  AAC  TCG  CAG  CTC  ATC  CGC  TAC  GCG  GGC  TAC           1854
His  Asp  Phe  Arg  Val  Trp  Asn  Ser  Gln  Leu  Ile  Arg  Tyr  Ala  Gly  Tyr
470                        475                        480                        485

AAG  CAG  CCA  GAT  GGC  TCT  ACC  TTG  GGG  GAT  CCA  GCC  AAT  GTG  CAG  TTC           1902
Lys  Gln  Pro  Asp  Gly  Ser  Thr  Leu  Gly  Asp  Pro  Ala  Asn  Val  Gln  Phe
                    490                        495                        500

ACG  GAG  ATC  TGT  ATA  CAG  CAG  GGC  TGG  AAA  GCC  CCA  AGA  GGC  CGC  TTC           1950
Thr  Glu  Ile  Cys  Ile  Gln  Gln  Gly  Trp  Lys  Ala  Pro  Arg  Gly  Arg  Phe
               505                        510                        515

GAC  GTG  CTG  CCT  CTC  CTG  CTT  CAG  GCC  AAT  GGC  AAT  GAC  CCT  GAG  CTC           1998
Asp  Val  Leu  Pro  Leu  Leu  Leu  Gln  Ala  Asn  Gly  Asn  Asp  Pro  Glu  Leu
          520                        525                        530

TTC  CAG  ATC  CCC  CCA  GAG  CTG  GTG  CTG  GAA  GTG  CCC  ATC  AGG  CAC  CCC           2046
Phe  Gln  Ile  Pro  Pro  Glu  Leu  Val  Leu  Glu  Val  Pro  Ile  Arg  His  Pro
     535                        540                        545

AAG  TTC  GAC  TGG  TTT  AAG  GAC  CTG  GGG  CTC  AAA  TGG  TAT  GGC  CTC  CCC           2094
Lys  Phe  Asp  Trp  Phe  Lys  Asp  Leu  Gly  Leu  Lys  Trp  Tyr  Gly  Leu  Pro
550                        555                        560                        565
```

| | | | | | | | | | | | | | | | | |
|---|---|---|---|---|---|---|---|---|---|---|---|---|---|---|---|---|
| GCT | GTG | TCC | AAC | ATG | CTG | CTG | GAG | ATC | GGG | GGC | CTG | GAG | TTC | AGC | GCC | 2142 |
| Ala | Val | Ser | Asn | Met 570 | Leu | Leu | Glu | Ile 575 | Gly | Gly | Leu | Glu | Phe | Ser 580 | Ala | |
| TGT | CCC | TTC | AGC | GGC | TGG | TAC | ATG | GGC | ACA | GAG | ATC | GGC | GTC | CGT | GAC | 2190 |
| Cys | Pro | Phe | Ser 585 | Gly | Trp | Tyr | Met | Gly 590 | Thr | Glu | Ile | Gly | Val 595 | Arg | Asp | |
| TAC | TGT | GAC | AAC | TCT | CGA | TAC | AAC | ATC | CTG | GAG | GAA | GTA | GCC | AAG | AAG | 2238 |
| Tyr | Cys | Asp 600 | Asn | Ser | Arg | Tyr | Asn 605 | Ile | Leu | Glu | Glu | Val 610 | Ala | Lys | Lys | |
| ATG | GAT | TTG | GAC | ATG | AGG | AAG | ACC | TCG | TCC | CTC | TGG | AAG | GAC | CAA | GCA | 2286 |
| Met | Asp 615 | Leu | Asp | Met | Arg | Lys 620 | Thr | Ser | Ser | Leu | Trp 625 | Lys | Asp | Gln | Ala | |
| CTG | GTG | GAG | ATC | AAC | ATT | GCT | GTT | CTA | TAT | AGC | TTC | CAG | AGT | GAC | AAG | 2334 |
| Leu 630 | Val | Glu | Ile | Asn 635 | Ile | Ala | Val | Leu | Tyr 640 | Ser | Phe | Gln | Ser | Asp 645 | Lys | |
| GTG | ACC | ATC | GTT | GAC | CAC | CAC | TCT | GCC | ACG | GAG | TCC | TTC | ATC | AAA | CAC | 2382 |
| Val | Thr | Ile | Val | Asp 650 | His | His | Ser | Ala | Thr 655 | Glu | Ser | Phe | Ile | Lys 660 | His | |
| ATG | GAG | AAT | GAA | TAC | CGC | TGC | AGA | GGG | GGC | TGC | CCC | GCC | GAC | TGG | GTG | 2430 |
| Met | Glu | Asn | Glu 665 | Tyr | Arg | Cys | Arg | Gly 670 | Gly | Cys | Pro | Ala | Asp 675 | Trp | Val | |
| TGG | ATT | GTG | CCT | CCC | ATG | TCG | GGC | AGC | ATC | ACC | CCT | GTC | TTC | CAC | CAG | 2478 |
| Trp | Ile | Val 680 | Pro | Pro | Met | Ser | Gly 685 | Ser | Ile | Thr | Pro | Val 690 | Phe | His | Gln | |
| GAG | ATG | CTC | AAC | TAT | AGA | CTC | ACC | CCG | TCC | TTT | GAA | TAC | CAG | CCT | GAT | 2526 |
| Glu | Met | Leu | Asn 695 | Tyr | Arg | Leu | Thr | Pro 700 | Ser | Phe | Glu | Tyr | Gln 705 | Pro | Asp | |
| CCA | TGG | AAC | ACC | CAC | GTG | TGG | AAG | GGC | ACC | AAC | GGG | ACC | CCC | ACG | AAG | 2574 |
| Pro 710 | Trp | Asn | Thr | His | Val 715 | Trp | Lys | Gly | Thr | Asn 720 | Gly | Thr | Pro | Thr | Lys 725 | |
| CGG | CGA | GCT | ATC | GGC | TTT | AAG | AAA | TTG | GCA | GAG | GCC | GTC | AAG | TTC | TCA | 2622 |
| Arg | Arg | Ala | Ile | Gly 730 | Phe | Lys | Lys | Leu | Ala 735 | Glu | Ala | Val | Lys | Phe 740 | Ser | |
| GCC | AAG | CTA | ATG | GGG | CAG | GCC | ATG | GCC | AAG | AGG | GTC | AAG | GCG | ACC | ATT | 2670 |
| Ala | Lys | Leu | Met 745 | Gly | Gln | Ala | Met | Ala 750 | Lys | Arg | Val | Lys | Ala 755 | Thr | Ile | |
| CTC | TAC | GCC | ACA | GAG | ACA | GGC | AAA | TCA | CAA | GCC | TAT | GCC | AAG | ACC | CTG | 2718 |
| Leu | Tyr | Ala 760 | Thr | Glu | Thr | Gly | Lys 765 | Ser | Gln | Ala | Tyr | Ala 770 | Lys | Thr | Leu | |
| TGT | GAG | ATC | TTC | AAG | CAC | GCC | TTC | GAT | GCC | AAG | GCA | ATG | TCC | ATG | GAG | 2766 |
| Cys | Glu | Ile | Phe 775 | Lys | His | Ala | Phe | Asp 780 | Ala | Lys | Ala | Met | Ser 785 | Met | Glu | |
| GAG | TAT | GAC | ATC | GTG | CAC | CTG | GAG | CAC | GAA | GCC | CTG | GTC | TTG | GTG | GTC | 2814 |
| Glu 790 | Tyr | Asp | Ile | Val | His 795 | Leu | Glu | His | Glu | Ala 800 | Leu | Val | Leu | Val | Val 805 | |
| ACC | AGC | ACC | TTT | GGC | AAT | GGA | GAC | CCC | CCT | GAG | AAC | GGG | GAG | AAA | TTC | 2862 |
| Thr | Ser | Thr | Phe | Gly 810 | Asn | Gly | Asp | Pro | Pro 815 | Glu | Asn | Gly | Glu | Lys 820 | Phe | |
| GGC | TGT | GCT | TTA | ATG | GAG | ATG | AGG | CAC | CCC | AAC | TCT | GTG | CAG | GAG | GAG | 2910 |
| Gly | Cys | Ala | Leu | Met 825 | Glu | Met | Arg | His | Pro 830 | Asn | Ser | Val | Gln | Glu 835 | Glu | |
| AGA | AAG | AGC | TAC | AAG | GTC | CGA | TTC | AAC | AGC | GTC | TCC | TCC | TAT | TCT | GAC | 2958 |
| Arg | Lys | Ser | Tyr | Lys 840 | Val | Arg | Phe | Asn | Ser 845 | Val | Ser | Ser | Tyr | Ser 850 | Asp | |
| TCC | CGA | AAG | TCA | TCG | GGC | GAC | GGA | CCC | GAC | CTC | AGA | GAC | AAC | TTT | GAA | 3006 |
| Ser | Arg | Lys | Ser 855 | Ser | Gly | Asp | Gly | Pro 860 | Asp | Leu | Arg | Asp | Asn 865 | Phe | Glu | |
| AGT | ACT | GGA | CCC | CTG | GCC | AAT | GTG | AGG | TTC | TCA | GTG | TTC | GGC | CTC | GGC | 3054 |
| Ser | Thr | Gly | Pro 870 | Leu | Ala | Asn | Val | Arg 875 | Phe | Ser | Val | Phe | Gly 880 | Leu | Gly 885 | |
| TCT | CGG | GCG | TAC | CCC | CAC | TTC | TGT | GCC | TTT | GGG | CAT | GCG | GTG | GAC | ACC | 3102 |
| Ser | Arg | Ala | Tyr | Pro | His | Phe | Cys | Ala | Phe | Gly | His | Ala | Val | Asp | Thr | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 890 |     |     |     |     | 895 |     |     |     |     | 900 |      |
| CTC | CTG | GAG | GAA | CTG | GGA | GGG | GAG | AGG | ATT | CTG | AAG | ATG | AGG | GAG | GGG | 3150 |
| Leu | Leu | Glu | Glu | Leu | Gly | Gly | Glu | Arg | Ile | Leu | Lys | Met | Arg | Glu | Gly |      |
|     |     |     |     | 905 |     |     |     |     | 910 |     |     |     |     | 915 |     |      |
| GAT | GAG | CTT | TGC | GGA | CAG | GAA | GAA | GCT | TTC | AGG | ACC | TGG | GCC | AAG | AAA | 3198 |
| Asp | Glu | Leu | Cys | Gly | Gln | Glu | Glu | Ala | Phe | Arg | Thr | Trp | Ala | Lys | Lys |      |
|     |     |     | 920 |     |     |     |     | 925 |     |     |     |     | 930 |     |     |      |
| GTC | TTC | AAG | GCA | GCC | TGT | GAT | GTG | TTC | TGC | GTG | GGG | GAT | GAC | GTC | AAC | 3246 |
| Val | Phe | Lys | Ala | Ala | Cys | Asp | Val | Phe | Cys | Val | Gly | Asp | Asp | Val | Asn |      |
|     |     | 935 |     |     |     |     | 940 |     |     |     |     | 945 |     |     |     |      |
| ATC | GAG | AAG | CCG | AAC | AAC | TCC | CTC | ATT | AGC | AAT | GAC | CGA | AGC | TGG | AAG | 3294 |
| Ile | Glu | Lys | Pro | Asn | Asn | Ser | Leu | Ile | Ser | Asn | Asp | Arg | Ser | Trp | Lys |      |
| 950 |     |     |     |     | 955 |     |     |     |     | 960 |     |     |     |     | 965 |      |
| AGG | AAC | AAG | TTC | CGC | CTC | ACG | TAT | GTG | GCG | GAA | GCT | CCA | GAT | CTG | ACC | 3342 |
| Arg | Asn | Lys | Phe | Arg | Leu | Thr | Tyr | Val | Ala | Glu | Ala | Pro | Asp | Leu | Thr |      |
|     |     |     |     | 970 |     |     |     |     | 975 |     |     |     |     | 980 |     |      |
| CAA | GGT | CTT | TCC | AAT | GTT | CAC | AAA | AAA | CGA | GTC | TCG | GCT | GCT | CGA | CTC | 3390 |
| Gln | Gly | Leu | Ser | Asn | Val | His | Lys | Lys | Arg | Val | Ser | Ala | Ala | Arg | Leu |      |
|     |     |     | 985 |     |     |     |     | 990 |     |     |     |     | 995 |     |     |      |
| CTC | AGC | CGC | CAA | AAC | CTG | CAA | AGC | CCT | AAG | TTC | AGC | CGA | TCG | ACC | ATC | 3438 |
| Leu | Ser | Arg | Gln | Asn | Leu | Gln | Ser | Pro | Lys | Phe | Ser | Arg | Ser | Thr | Ile |      |
|     |     | 1000|     |     |     |     | 1005|     |     |     |     | 1010|     |     |     |      |
| TTC | GTG | CGT | CTC | CAC | ACC | AAC | GGG | AAT | CAG | GAG | CTG | CAG | TAC | CAG | CCA | 3486 |
| Phe | Val | Arg | Leu | His | Thr | Asn | Gly | Asn | Gln | Glu | Leu | Gln | Tyr | Gln | Pro |      |
| 1015|     |     |     |     | 1020|     |     |     |     | 1025|     |     |     |     |     |      |
| GGG | GAC | CAC | CTG | GGT | GTC | TTC | CCC | GGC | AAC | CAC | GAG | GAC | CTC | GTG | AAT | 3534 |
| Gly | Asp | His | Leu | Gly | Val | Phe | Pro | Gly | Asn | His | Glu | Asp | Leu | Val | Asn |      |
| 1030|     |     |     |     | 1035|     |     |     |     | 1040|     |     |     |     | 1045|      |
| GCA | CTC | ATT | GAA | CGG | CTG | GAG | GAT | GCA | CCG | CCT | GCC | AAC | CAC | GTG | GTG | 3582 |
| Ala | Leu | Ile | Glu | Arg | Leu | Glu | Asp | Ala | Pro | Pro | Ala | Asn | His | Val | Val |      |
|     |     |     |     | 1050|     |     |     |     | 1055|     |     |     |     | 1060|     |      |
| AAG | GTG | GAG | ATG | CTG | GAG | GAG | AGG | AAC | ACT | GCT | CTG | GGT | GTC | ATC | AGT | 3630 |
| Lys | Val | Glu | Met | Leu | Glu | Glu | Arg | Asn | Thr | Ala | Leu | Gly | Val | Ile | Ser |      |
|     |     |     |     | 1065|     |     |     |     | 1070|     |     |     |     | 1075|     |      |
| AAT | TGG | AAG | GAT | GAA | TCT | CGC | CTC | CCA | CCC | TGC | ACC | ATC | TTC | CAG | GCC | 3678 |
| Asn | Trp | Lys | Asp | Glu | Ser | Arg | Leu | Pro | Pro | Cys | Thr | Ile | Phe | Gln | Ala |      |
|     |     |     | 1080|     |     |     |     | 1085|     |     |     |     | 1090|     |     |      |
| TTC | AAG | TAC | TAC | CTG | GAC | ATC | ACC | ACG | CCG | CCC | ACG | CCC | CTG | CAG | CTG | 3726 |
| Phe | Lys | Tyr | Tyr | Leu | Asp | Ile | Thr | Thr | Pro | Pro | Thr | Pro | Leu | Gln | Leu |      |
|     |     | 1095|     |     |     |     | 1100|     |     |     |     | 1105|     |     |     |      |
| CAG | CAG | TTC | GCC | TCT | CTG | GCC | ACT | AAT | GAG | AAA | GAG | AAG | CAG | CGG | TTG | 3774 |
| Gln | Gln | Phe | Ala | Ser | Leu | Ala | Thr | Asn | Glu | Lys | Glu | Lys | Gln | Arg | Leu |      |
| 1110|     |     |     |     | 1115|     |     |     |     | 1120|     |     |     |     | 1125|      |
| CTG | GTC | CTC | AGC | AAG | GGG | CTC | CAG | GAA | TAT | GAG | GAG | TGG | AAG | TGG | GGC | 3822 |
| Leu | Val | Leu | Ser | Lys | Gly | Leu | Gln | Glu | Tyr | Glu | Glu | Trp | Lys | Trp | Gly |      |
|     |     |     |     | 1130|     |     |     |     | 1135|     |     |     |     | 1140|     |      |
| AAG | AAC | CCC | ACA | ATG | GTG | GAG | GTG | CTG | GAG | GAG | TTC | CCG | TCC | ATC | CAG | 3870 |
| Lys | Asn | Pro | Thr | Met | Val | Glu | Val | Leu | Glu | Glu | Phe | Pro | Ser | Ile | Gln |      |
|     |     |     |     | 1145|     |     |     |     | 1150|     |     |     |     | 1155|     |      |
| ATG | CCG | GCT | ACA | CTT | CTC | CTC | ACT | CAG | CTG | TCG | CTG | CTG | CAG | CCT | CGC | 3918 |
| Met | Pro | Ala | Thr | Leu | Leu | Leu | Thr | Gln | Leu | Ser | Leu | Leu | Gln | Pro | Arg |      |
|     |     |     | 1160|     |     |     |     | 1165|     |     |     |     | 1170|     |     |      |
| TAC | TAC | TCC | ATC | AGC | TCC | TCT | CCA | GAC | ATG | TAC | CCC | GAC | GAG | GTG | CAC | 3966 |
| Tyr | Tyr | Ser | Ile | Ser | Ser | Ser | Pro | Asp | Met | Tyr | Pro | Asp | Glu | Val | His |      |
|     |     |     | 1175|     |     |     |     | 1180|     |     |     |     | 1185|     |     |      |
| CTC | ACT | GTG | GCC | ATC | GTC | TCC | TAC | CAC | ACC | CGA | GAC | GGA | GAA | GGA | CCA | 4014 |
| Leu | Thr | Val | Ala | Ile | Val | Ser | Tyr | His | Thr | Arg | Asp | Gly | Glu | Gly | Pro |      |
| 1190|     |     |     |     | 1195|     |     |     |     | 1200|     |     |     |     | 1205|      |
| GTC | CAC | CAC | GGG | GTG | TGC | TCC | TCC | TGG | CTC | AAC | AGA | ATA | CAG | GCT | GAC | 4062 |
| Val | His | His | Gly | Val | Cys | Ser | Ser | Trp | Leu | Asn | Arg | Ile | Gln | Ala | Asp |      |
|     |     |     |     | 1210|     |     |     |     | 1215|     |     |     |     | 1220|     |      |

```
GAT GTA GTC CCC TGC TTC GTG AGA GGT GCC CCT AGC TTC CAC CTG CCT        4110
Asp Val Val Pro Cys Phe Val Arg Gly Ala Pro Ser Phe His Leu Pro
            1225                1230                1235

CGA AAC CCC CAG GTG CCT TGC ATC CTG GTT GGC CCA GGC ACT GGC ATC        4158
Arg Asn Pro Gln Val Pro Cys Ile Leu Val Gly Pro Gly Thr Gly Ile
        1240                1245                1250

GCA CCC TTC CGA AGC TTC TGG CAA CAG CGA CAA TTT GAC ATC CAA CAC        4206
Ala Pro Phe Arg Ser Phe Trp Gln Gln Arg Gln Phe Asp Ile Gln His
    1255                1260                1265

AAA GGA ATG AAT CCG TGC CCC ATG GTT CTG GTC TTC GGG TGT CGA CAA        4254
Lys Gly Met Asn Pro Cys Pro Met Val Leu Val Phe Gly Cys Arg Gln
1270                1275                1280                1285

TCC AAG ATA GAT CAT ATC TAC AGA GAG GAG ACC CTG CAG GCT AAG AAC        4302
Ser Lys Ile Asp His Ile Tyr Arg Glu Glu Thr Leu Gln Ala Lys Asn
            1290                1295                1300

AAG GGC GTC TTC AGA GAG CTG TAC ACT GCC TAT TCC CGG GAA CCG GAC        4350
Lys Gly Val Phe Arg Glu Leu Tyr Thr Ala Tyr Ser Arg Glu Pro Asp
        1305                1310                1315

AGG CCA AAG AAA TAT GTA CAG GAC GTG CTG CAG GAA CAG CTG GCT GAG        4398
Arg Pro Lys Lys Tyr Val Gln Asp Val Leu Gln Glu Gln Leu Ala Glu
    1320                1325                1330

TCT GTG TAC CGC GCC CTG AAG GAG CAA GGA GGC CAC ATT TAT GTC TGT        4446
Ser Val Tyr Arg Ala Leu Lys Glu Gln Gly Gly His Ile Tyr Val Cys
1335                1340                1345

GGG GAC GTT ACC ATG GCC GCC GAT GTC CTC AAA GCC ATC CAG CGC ATA        4494
Gly Asp Val Thr Met Ala Ala Asp Val Leu Lys Ala Ile Gln Arg Ile
1350                1355                1360                1365

ATG ACC CAG CAG GGG AAA CTC TCA GAG GAG GAC GCT GGT GTA TTC ATC        4542
Met Thr Gln Gln Gly Lys Leu Ser Glu Glu Asp Ala Gly Val Phe Ile
            1370                1375                1380

AGC AGG CTG AGG GAT GAC AAC CGG TAC CAC GAG GAC ATC TTT GGA GTC        4590
Ser Arg Leu Arg Asp Asp Asn Arg Tyr His Glu Asp Ile Phe Gly Val
        1385                1390                1395

ACC CTC AGA ACG TAT GAA GTG ACC AAC CGC CTT AGA TCT GAG TCC ATC        4638
Thr Leu Arg Thr Tyr Glu Val Thr Asn Arg Leu Arg Ser Glu Ser Ile
    1400                1405                1410

GCC TTC ATC GAA GAG AGC AAA AAA GAC GCA GAT GAG GTT TTC AGC TCC        4686
Ala Phe Ile Glu Glu Ser Lys Lys Asp Ala Asp Glu Val Phe Ser Ser
    1415                1420                1425

TAACTGGATC CTCCTGCCCC CGTGCGTGCG ATGTGGCGGC TGCCCCAAGT GCCCAAGTAA     4746

GGGCGGCCGC AGGTTGACTA AATTCGGACA CACACGGCTG AACCGAGTGG CCCTGCTCTG     4806

CCTCTTGTCC TGTTGCTGTG TCCTGGTCCT TCTTCCTGCT CTGGGCTCTC TCAACCCCAC     4866

CCCTGGGTTT TCTCCTTGAC TCTTGGGCTA CGATGCATCA CCCTTGTACC CTGCAGTGGC     4926

TCTCACAAAA CCGCATCCTC CCCACCCCCA CCCGATTGCT GCCAAGGGCA GGTTGCGGTG     4986

CATGGCTGTT GCTCCTGTTG TTGGGGTCTG AAGGTGGCTG GCGCTGGGCC TCAGGTCACC     5046

CTGAACCAGT CCCTTGGCCA CTTAAGCCCC CTTCCACCCT CTTTTTATGA TGGTGTGTTT     5106

GT                                                                    5108
```

( 2 ) INFORMATION FOR SEQ ID NO:2:

( i ) SEQUENCE CHARACTERISTICS:
        ( A ) LENGTH: 1429 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Glu Asn Thr Phe Gly Val Gln Gln Ile Gln Pro Asn Val Ile
 1               5                  10                  15
```

```
Ser Val Arg Leu Phe Lys Arg Lys Val Gly Gly Leu Gly Phe Leu Val
         20                  25                  30

Lys Glu Arg Val Ser Lys Pro Pro Val Ile Ile Ser Asp Leu Ile Arg
             35                  40                  45

Gly Gly Ala Ala Glu Gln Ser Gly Leu Ile Gln Ala Gly Asp Ile Ile
         50                  55                  60

Leu Ala Val Asn Asp Arg Pro Leu Val Asp Leu Ser Tyr Asp Ser Ala
 65                  70                  75                  80

Leu Glu Val Leu Arg Gly Ile Ala Ser Glu Thr His Val Val Leu Ile
                 85                  90                  95

Leu Arg Gly Pro Glu Gly Phe Thr Thr His Leu Glu Thr Thr Phe Thr
             100                 105                 110

Gly Asp Gly Thr Pro Lys Thr Ile Arg Val Thr Gln Pro Leu Gly Pro
             115                 120                 125

Pro Thr Lys Ala Val Asp Leu Ser His Gln Pro Ser Ala Ser Lys Asp
             130                 135                 140

Gln Ser Leu Ala Val Asp Arg Val Thr Gly Leu Gly Asn Gly Pro Gln
145                 150                 155                 160

His Ala Gln Gly His Gly Gln Gly Ala Gly Ser Val Ser Gln Ala Asn
                 165                 170                 175

Gly Val Ala Ile Asp Pro Thr Met Lys Ser Thr Lys Ala Asn Leu Gln
             180                 185                 190

Asp Ile Gly Glu His Asp Glu Leu Leu Lys Glu Ile Glu Pro Val Leu
             195                 200                 205

Ser Ile Leu Asn Ser Gly Ser Lys Ala Thr Asn Arg Gly Gly Pro Ala
             210                 215                 220

Lys Ala Glu Met Lys Asp Thr Gly Ile Gln Val Asp Arg Asp Leu Asp
225                 230                 235                 240

Gly Lys Ser His Lys Ala Pro Pro Leu Gly Gly Asp Asn Asp Arg Val
                 245                 250                 255

Phe Asn Asp Leu Trp Gly Lys Asp Asn Val Pro Val Ile Leu Asn Asn
             260                 265                 270

Pro Tyr Ser Glu Lys Glu Gln Ser Pro Thr Ser Gly Lys Gln Ser Pro
         275                 280                 285

Thr Lys Asn Gly Ser Pro Ser Arg Cys Pro Arg Phe Leu Lys Val Lys
     290                 295                 300

Asn Trp Glu Thr Asp Val Val Leu Thr Asp Thr Leu His Leu Lys Ser
305                 310                 315                 320

Thr Leu Glu Thr Gly Cys Thr Glu His Ile Cys Met Gly Ser Ile Met
                 325                 330                 335

Leu Pro Ser Gln His Thr Arg Lys Pro Glu Asp Val Arg Thr Lys Asp
             340                 345                 350

Gln Leu Phe Pro Leu Ala Lys Glu Phe Leu Asp Gln Tyr Tyr Ser Ser
         355                 360                 365

Ile Lys Arg Phe Gly Ser Lys Ala His Met Asp Arg Leu Glu Glu Val
     370                 375                 380

Asn Lys Glu Ile Glu Ser Thr Ser Thr Tyr Gln Leu Lys Asp Thr Glu
385                 390                 395                 400

Leu Ile Tyr Gly Ala Lys His Ala Trp Arg Asn Ala Ser Arg Cys Val
             405                 410                 415

Gly Arg Ile Gln Trp Ser Lys Leu Gln Val Phe Asp Ala Arg Asp Cys
             420                 425                 430

Thr Thr Ala His Gly Met Phe Asn Tyr Ile Cys Asn His Val Lys Tyr
             435                 440                 445
```

-continued

| | | | | | | | | | | | | | | |
|---|---|---|---|---|---|---|---|---|---|---|---|---|---|---|
| Ala | Thr | Asn | Lys | Gly | Asn | Leu | Arg | Ser | Ala | Ile | Thr | Ile | Phe | Pro | Gln |
| | 450 | | | | 455 | | | | | 460 | | | | | |
| Arg | Thr | Asp | Gly | Lys | His | Asp | Phe | Arg | Val | Trp | Asn | Ser | Gln | Leu | Ile |
| 465 | | | | | 470 | | | | 475 | | | | | 480 | |
| Arg | Tyr | Ala | Gly | Tyr | Lys | Gln | Pro | Asp | Gly | Ser | Thr | Leu | Gly | Asp | Pro |
| | | | | 485 | | | | 490 | | | | | 495 | | |
| Ala | Asn | Val | Gln | Phe | Thr | Glu | Ile | Cys | Ile | Gln | Gln | Gly | Trp | Lys | Ala |
| | | | 500 | | | | | 505 | | | | | 510 | | |
| Pro | Arg | Gly | Arg | Phe | Asp | Val | Leu | Pro | Leu | Leu | Leu | Gln | Ala | Asn | Gly |
| | | 515 | | | | | 520 | | | | | 525 | | | |
| Asn | Asp | Pro | Glu | Leu | Phe | Gln | Ile | Pro | Pro | Glu | Leu | Val | Leu | Glu | Val |
| | 530 | | | | | 535 | | | | | 540 | | | | |
| Pro | Ile | Arg | His | Pro | Lys | Phe | Asp | Trp | Phe | Lys | Asp | Leu | Gly | Leu | Lys |
| 545 | | | | | 550 | | | | | 555 | | | | | 560 |
| Trp | Tyr | Gly | Leu | Pro | Ala | Val | Ser | Asn | Met | Leu | Leu | Glu | Ile | Gly | Gly |
| | | | | 565 | | | | | 570 | | | | | 575 | |
| Leu | Glu | Phe | Ser | Ala | Cys | Pro | Phe | Ser | Gly | Trp | Tyr | Met | Gly | Thr | Glu |
| | | | 580 | | | | | 585 | | | | | 590 | | |
| Ile | Gly | Val | Arg | Asp | Tyr | Cys | Asp | Asn | Ser | Arg | Tyr | Asn | Ile | Leu | Glu |
| | | | 595 | | | | 600 | | | | | 605 | | | |
| Glu | Val | Ala | Lys | Lys | Met | Asp | Leu | Asp | Met | Arg | Lys | Thr | Ser | Ser | Leu |
| | 610 | | | | | 615 | | | | | 620 | | | | |
| Trp | Lys | Asp | Gln | Ala | Leu | Val | Glu | Ile | Asn | Ile | Ala | Val | Leu | Tyr | Ser |
| 625 | | | | | 630 | | | | | 635 | | | | | 640 |
| Phe | Gln | Ser | Asp | Lys | Val | Thr | Ile | Val | Asp | His | His | Ser | Ala | Thr | Glu |
| | | | | 645 | | | | | 650 | | | | | 655 | |
| Ser | Phe | Ile | Lys | His | Met | Glu | Asn | Glu | Tyr | Arg | Cys | Arg | Gly | Gly | Cys |
| | | | 660 | | | | | 665 | | | | | 670 | | |
| Pro | Ala | Asp | Trp | Val | Trp | Ile | Val | Pro | Pro | Met | Ser | Gly | Ser | Ile | Thr |
| | | | 675 | | | | 680 | | | | | 685 | | | |
| Pro | Val | Phe | His | Gln | Glu | Met | Leu | Asn | Tyr | Arg | Leu | Thr | Pro | Ser | Phe |
| | 690 | | | | | 695 | | | | | 700 | | | | |
| Glu | Tyr | Gln | Pro | Asp | Pro | Trp | Asn | Thr | His | Val | Trp | Lys | Gly | Thr | Asn |
| 705 | | | | | 710 | | | | | 715 | | | | | 720 |
| Gly | Thr | Pro | Thr | Lys | Arg | Arg | Ala | Ile | Gly | Phe | Lys | Lys | Leu | Ala | Glu |
| | | | | 725 | | | | | 730 | | | | | 735 | |
| Ala | Val | Lys | Phe | Ser | Ala | Lys | Leu | Met | Gly | Gln | Ala | Met | Ala | Lys | Arg |
| | | | 740 | | | | | 745 | | | | | 750 | | |
| Val | Lys | Ala | Thr | Ile | Leu | Tyr | Ala | Thr | Glu | Thr | Gly | Lys | Ser | Gln | Ala |
| | | 755 | | | | | 760 | | | | | 765 | | | |
| Tyr | Ala | Lys | Thr | Leu | Cys | Glu | Ile | Phe | Lys | His | Ala | Phe | Asp | Ala | Lys |
| | 770 | | | | | 775 | | | | | 780 | | | | |
| Ala | Met | Ser | Met | Glu | Glu | Tyr | Asp | Ile | Val | His | Leu | Glu | His | Glu | Ala |
| 785 | | | | | 790 | | | | | 795 | | | | | 800 |
| Leu | Val | Leu | Val | Val | Thr | Ser | Thr | Phe | Gly | Asn | Gly | Asp | Pro | Pro | Glu |
| | | | | 805 | | | | | 810 | | | | | 815 | |
| Asn | Gly | Glu | Lys | Phe | Gly | Cys | Ala | Leu | Met | Glu | Met | Arg | His | Pro | Asn |
| | | | 820 | | | | | 825 | | | | | 830 | | |
| Ser | Val | Gln | Glu | Glu | Arg | Lys | Ser | Tyr | Lys | Val | Arg | Phe | Asn | Ser | Val |
| | | | 835 | | | | | 840 | | | | | 845 | | |
| Ser | Ser | Tyr | Ser | Asp | Ser | Arg | Lys | Ser | Ser | Gly | Asp | Gly | Pro | Asp | Leu |
| | | 850 | | | | | 855 | | | | | 860 | | | |
| Arg | Asp | Asn | Phe | Glu | Ser | Thr | Gly | Pro | Leu | Ala | Asn | Val | Arg | Phe | Ser |
| 865 | | | | | 870 | | | | | 875 | | | | | 880 |
| Val | Phe | Gly | Leu | Gly | Ser | Arg | Ala | Tyr | Pro | His | Phe | Cys | Ala | Phe | Gly |

|     |     |     | 885 |     |     |     |     | 890 |     |     |     |     | 895 |     |
| --- | --- | --- | --- | --- | --- | --- | --- | --- | --- | --- | --- | --- | --- | --- |

His Ala Val Asp Thr Leu Leu Glu Glu Leu Gly Gly Glu Arg Ile Leu
            900                     905                     910

Lys Met Arg Glu Gly Asp Glu Leu Cys Gly Gln Glu Ala Phe Arg
            915                     920                     925

Thr Trp Ala Lys Lys Val Phe Lys Ala Ala Cys Asp Val Phe Cys Val
        930                     935                     940

Gly Asp Asp Val Asn Ile Glu Lys Pro Asn Asn Ser Leu Ile Ser Asn
945                     950                     955                     960

Asp Arg Ser Trp Lys Arg Asn Lys Phe Arg Leu Thr Tyr Val Ala Glu
            965                     970                     975

Ala Pro Asp Leu Thr Gln Gly Leu Ser Asn Val His Lys Lys Arg Val
            980                     985                     990

Ser Ala Ala Arg Leu Leu Ser Arg Gln Asn Leu Gln Ser Pro Lys Phe
            995                     1000                    1005

Ser Arg Ser Thr Ile Phe Val Arg Leu His Thr Asn Gly Asn Gln Glu
            1010                    1015                    1020

Leu Gln Tyr Gln Pro Gly Asp His Leu Gly Val Phe Pro Gly Asn His
1025                    1030                    1035                    1040

Glu Asp Leu Val Asn Ala Leu Ile Glu Arg Leu Glu Asp Ala Pro Pro
            1045                    1050                    1055

Ala Asn His Val Val Lys Val Glu Met Leu Glu Glu Arg Asn Thr Ala
            1060                    1065                    1070

Leu Gly Val Ile Ser Asn Trp Lys Asp Glu Ser Arg Leu Pro Pro Cys
            1075                    1080                    1085

Thr Ile Phe Gln Ala Phe Lys Tyr Tyr Leu Asp Ile Thr Thr Pro Pro
            1090                    1095                    1100

Thr Pro Leu Gln Leu Gln Gln Phe Ala Ser Leu Ala Thr Asn Glu Lys
1105                    1110                    1115                    1120

Glu Lys Gln Arg Leu Leu Val Leu Ser Lys Gly Leu Gln Glu Tyr Glu
            1125                    1130                    1135

Glu Trp Lys Trp Gly Lys Asn Pro Thr Met Val Glu Val Leu Glu Glu
            1140                    1145                    1150

Phe Pro Ser Ile Gln Met Pro Ala Thr Leu Leu Leu Thr Gln Leu Ser
            1155                    1160                    1165

Leu Leu Gln Pro Arg Tyr Tyr Ser Ile Ser Ser Ser Pro Asp Met Tyr
            1170                    1175                    1180

Pro Asp Glu Val His Leu Thr Val Ala Ile Val Ser Tyr His Thr Arg
1185                    1190                    1195                    1200

Asp Gly Glu Gly Pro Val His His Gly Val Cys Ser Ser Trp Leu Asn
            1205                    1210                    1215

Arg Ile Gln Ala Asp Asp Val Val Pro Cys Phe Val Arg Gly Ala Pro
            1220                    1225                    1230

Ser Phe His Leu Pro Arg Asn Pro Gln Val Pro Cys Ile Leu Val Gly
            1235                    1240                    1245

Pro Gly Thr Gly Ile Ala Pro Phe Arg Ser Phe Trp Gln Gln Arg Gln
            1250                    1255                    1260

Phe Asp Ile Gln His Lys Gly Met Asn Pro Cys Pro Met Val Leu Val
1265                    1270                    1275                    1280

Phe Gly Cys Arg Gln Ser Lys Ile Asp His Ile Tyr Arg Glu Glu Thr
            1285                    1290                    1295

Leu Gln Ala Lys Asn Lys Gly Val Phe Arg Glu Leu Tyr Thr Ala Tyr
            1300                    1305                    1310

Ser Arg Glu Pro Asp Arg Pro Lys Lys Tyr Val Gln Asp Val Leu Gln
            1315                    1320                    1325

```
Glu Gln Leu Ala Glu Ser Val Tyr Arg Ala Leu Lys Glu Gln Gly Gly
    1330            1335               1340

His Ile Tyr Val Cys Gly Asp Val Thr Met Ala Ala Asp Val Leu Lys
1345                1350            1355               1360

Ala Ile Gln Arg Ile Met Thr Gln Gln Gly Lys Leu Ser Glu Glu Asp
                1365            1370               1375

Ala Gly Val Phe Ile Ser Arg Leu Arg Asp Asp Asn Arg Tyr His Glu
            1380            1385               1390

Asp Ile Phe Gly Val Thr Leu Arg Thr Tyr Glu Val Thr Asn Arg Leu
        1395            1400           1405

Arg Ser Glu Ser Ile Ala Phe Ile Glu Glu Ser Lys Lys Asp Ala Asp
    1410            1415              1420

Glu Val Phe Ser Ser
1425
```

PURIFICATION AND MOLECULAR CLONING OF NITRIC OXIDE SYNTHASE

This invention was made with government support under grants MH-18501 and DA-00074 awarded by the United States Public Health Service and the Department of Health and Human Services. The government has certain rights in the invention.

BACKGROUND OF THE INVENTION

Endothelium-derived relaxing factor, a labile substance formed by endothelial cells, which mediates vasodilation, has been shown to be identical to nitric oxide (NO) (Moncada et al., (1988) *Biochem. Pharmacol.* 37, pp. 2495–2501; Furchgott et al., (1988) *FASEB J.* 3, pp. 2007–2018; and Ignarro, L. J. (1989) *FASEB J.* 3, pp. 31–36). In addition to relaxing blood vessels, NO has multiple messenger functions as has been demonstrated in macrophages (Marletta et al., (1988) *Biochemistry* 27, pp. 8706–8711) and in brain tissue (Garthwaite et al., (1988) *Nature* 336, pp. 385–388; Knowles et al., (1989) *Proc. Natl. Acad. Sci. USA*, 86, pp. 5159–5162; and Bredt et al., (1989) *Proc. Natl. Acad. Sci. USA*, 86, pp. 9030–9033). NO appears responsible for the cytotoxic effects of macrophages and neutrophils (Hibbs et al., (1987) *J. Immunol.*, 138, pp. 550–565).

Evidence that NO mediates functions of tissues as diverse as the brain, endothelium, and blood cells suggests a wide-spread role for NO as a messenger molecule. Localizing NO formation at a cellular level throughout the body would be greatly facilitated by immunohistochemical identification of NO synthase (NOS), the NO-forming enzyme. The use of NOS to supply deficient individuals with NO-forming ability would be expedited by the purification of the enzyme. In addition, the testing of populations for a genetic abnormality leading to deficient NO formation, such as in patients with migraines, hypertension, and coronary artery disease would be hastened by the isolation of the gene encoding NOS. Thus there is a need in the art for the biological tools for the characterization and manipulation of the NO-forming enzymatic apparatus.

SUMMARY OF THE INVENTION

It is an object of the invention to provide a method of purifying calmodulin-dependent NOS.

It is another object of the invention to provide a purified preparation of calmodulin-dependent NOS.

It is still another object of the invention to provide a preparation of antibodies which is immunoreactive with calmodulin-dependent NOS.

It is yet another object of the invention to provide a cDNA molecule which encodes all or a portion of calmodulin-dependent NOS.

These and other objects of the invention are provided by one or more of the embodiments which are described below. In one embodiment of the invention a method of purifying calmodulin-dependent NOS is provided, which comprises the steps of:

contacting a preparation comprising calmodulin-dependent NOS with a solid matrix comprising NADPH or an NADPH analog; and eluting calmodulin-dependent NOS from said solid matrix with NADPH or a soluble NADPH analog.

In another embodiment of the invention a purified preparation of calmodulin-dependent NOS is provided which has a specific activity of greater than about 500 nmoles citrulline/mg/min.

In yet another embodiment of the invention a preparation of antibodies is provided which is immunoreactive with brain-derived calmodulin-dependent NOS of a mammal but not with other proteins of said mammal, as determined by Western blotting.

In still another embodiment of the invention a cDNA molecule is provided which encodes all or a portion of calmodulin-dependent NOS, said molecule comprising between about 12 nucleotides and about 4,000 nucleotides.

The present invention provides the art with means to screen populations for genetic or acquired deficiencies in calmodulin-dependent NOS. In addition it provides the art with genes and proteins which can be used therapeutically to ameliorate the effects of genetic or acquired deficiencies in calmodulin-dependent NOS. The invention also provides a means of vasodilatation of blood vessels, for example those which may have become narrowed due to atherosclerosis.

BRIEF DESCRIPTION OF THE DRAWINGS

FIG. 3 shows an SDS/PAGE analysis of purified NO synthase. A 7.5% polyacrylamide gel was stained with Coomassie blue. Lanes: A, molecular mass markers (Myosin, 200 kDa); phosphorylase b, 97 kDA; bovine serum albumin, 68 kDA; ovalbumin, 43 kDA; carbonic anhydrase, 29 kDA; B, 30 µg of purified NO synthase. Silver staining displayed no additional protein bands with purified NO synthase.

DETAILED DESCRIPTION

Figure 1:
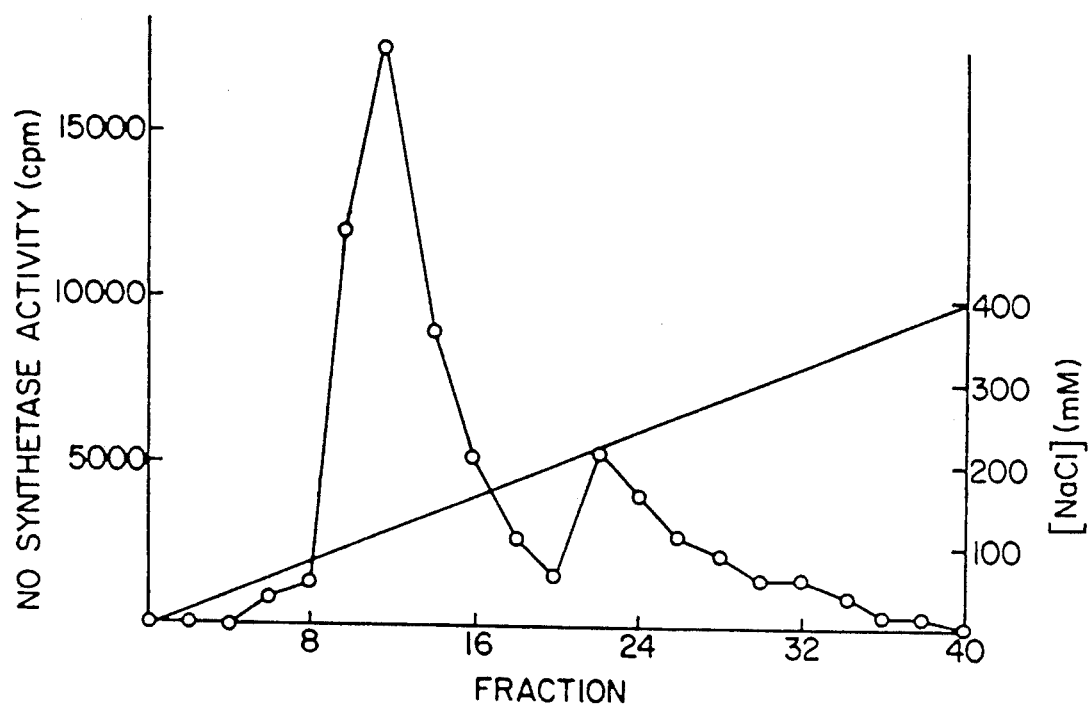
FIG. 1 shows a representative purification of NO synthase on DEAE-cellulose.

Nitric oxide synthase (EC #1.14.23) from brain has been purified to homogeneity, and its properties determined. It has been used to generate antibodies which have been used to localize the enzyme immunohistochemically. In addition, a cDNA encoding the NOS enzyme has been isolated and its sequence determined.

It is a finding of the present invention that NOS requires calmodulin for its enzyme activity. This contrasts with reported requirements of NOS isolated from activated macrophages, which require biopterins as a cofactor (Tayeh and Marletta; Kwon et al.). Macrophage-derived nitric oxide synthase has also been found to differ from that of brain-derived NOS immunochemically. Antisera raised against brain-derived NOS do not detect a similar sized protein in extracts of activated macrophages. The same antisera do, however, detect NOS in autonomic nerve fibers in the retina, in cell bodies and nerve fibers in the myenteric plexus of the intestine, in adrenal medulla, and in vascular endothelial cells. Thus it appears that there are at least two types of NOS proteins in mammalian tissues, one being calmodulin dependent and the other biopterin dependent.

According to the present invention, one can purify calmodulin-dependent NOS using column chromatography. Specifically, it has been found that greater than one-thousand-fold purification can be achieved using an affinity chromatography column. NADPH is a necessary cofactor for enzyme activity. If one employs a solid matrix containing an NADPH moiety or an NADPH analog, such as dextran blue, or 2',5'-ADP agarose or 2',5'-ADP sepharose, then the NOS of the present invention binds to the matrix. It can be eluted using a soluble form of NADPH or an analog thereof at a concentration of about 1 to about 10 mM. It is desirable that the preparation which is applied to the affinity chromatography column first be partially purified on an ion exchange column, such as, diethylaminoethyl (DEAE) cellulose. Other ion exchange columns known in the art can also be used. The NOS of the present invention binds to DEAE-cellulose and can be eluted with a sodium chloride gradient. The greatest peak of activity elutes with between about 70 mM and about 145 mM sodium chloride. Combination of these two column chromatography steps on a cleared brain homogenate results in a homogeneous preparation, as determined both by silver staining of an SDS/PAGE-separated sample, as well as by Western blotting.

Tissues which can be used as a source of calmodulin-dependent NOS include brain, endothelial cells of blood vessels, and adrenal glands. In addition, recombinant host cells containing cDNA clones of the NOS gene can be used as a source of NOS for purification according to the present invention. Collection and processing of tissues can be done as is known in the art. Typically tissues will be homogenized in buffers containing protease inhibitors. Debris can be removed from the homogenate by centrifugation at about 20,000×g for 15 minutes. Stability of the enzyme is enhanced by storage in bovine serum albumin (1 mg/ml)/20% (vol/vol) glycerol at −70° C. Stability is also enhanced in the presence of calmodulin.

Preparations of calmodulin-dependent NOS can be obtained which are homogeneous, according to techniques described above. Thus preparations having specific activities between about 500 and about 1000 nmol/mg/min are obtained. Preparations obtained according to the purification methods of the present invention are substantially free of contaminating proteins. Thus they are typically greater than 95% free of proteins of the same species source as the tissue from which they are extracted. Preferably, they are greater than 98% free of other proteins of the same species source. Using recombinant host cells to produce preparations of calmodulin-dependent NOS will also readily produce preparations which are substantially free of proteins of the same species source. Proteins which may be added back to a preparation to promote stability, such as calmodulin or bovine serum albumin, are not considered in the determination of purity. The presence of contaminating proteins can be determined using silver staining of polyacrylamide gels or Western blotting.

Antibody preparations are made according to techniques which are well known in the art. Both polyclonal and monoclonal antibodies are contemplated, production of both of which are well known. According to one method for obtaining a polyclonal antibody preparation, rabbits are immunized with a purified preparation of calmodulin-dependent NOS, as described above. The antiserum will preferably be affinity-purified by incubation with purified NOS and elution with 4M MgCl in 200 mM Tris-HCl buffer (pH 7.4). The eluate will desirably be dialysed against phosphate buffered saline with 0.1% Triton X100.

Antibodies can be used for immunohistochemical localization of NOS, or for quantitative assays on biological fluids or samples, such as in an enzyme-linked immunoadsorbent assay or radioimmunoassay. Such assays can determine if a tissue is producing an abnormally high or low amount of NOS.

cDNA molecules encoding calmodulin-dependent NOS are provided. The coding sequence of the gene is shown in SEQ ID NO:1. Whereas a particular nucleotide sequence is disclosed herein, other NOS-coding sequences are also encompassed by the invention, such as those which hybridize to the disclosed sequence, due to a difference in species source, allelic variations, or mutations introduced in the course of genetic manipulations. Thus other cDNA molecules which code for a closely related NOS are also contemplated. In addition, the cDNA molecule need not be complete in order to be useful. A portion of the cDNA can be used as a hybridization probe in order to quantitate mRNA expression, for example. Nucleotide probes are typically labeled with a detectable moiety such as a radioactive atom, or an enzyme. Whereas the entire gene-coding sequence is about 4 kb, sequences above about 12 to 15 nucleotides can be useful as hybridization probes. The cDNA sequence can also be used to hybridize to or amplify non-coding sequences. Thus the cDNA sequence can be used to isolate introns and regulatory regions important for expression in the body.

Portions of the disclosed sequence may also be used in polymerase chain reactions as primers. For example, primers can be used to amplify the NOS gene to determine if a mutation is present. The polymerase chain reaction is well known in the art.

EXAMPLES

EXAMPLE 1

This example describes the method by which NOS activity was assayed.

NO synthase activity was measured by monitoring the conversion of [$^3$H]arginine to [$^3$H]citrulline. For routine assays, we added 25 μl of enzyme extract and 25 μl of 100 nM [$^3$H]arginine to 100 μl of buffer containing 50 mM Hepes (pH 7.4), 1 mM NADPH, 1 mM EDTA, 1.25 mM CaCl$_2$, 1mM dithiothreitol, and 10 μg of calmodulin per ml. After incubation for 5 min at 22° C., assays were terminated with 2 ml of 20 mM Hepes, pH 5.5/2 mM EDTA, and were applied to 1-ml columns of Dowex AG502X-8 (Na$^+$ form), which were eluted with 2 ml of water. [$^3$H]Citrulline was quantified by liquid scintillation spectroscopy of the 4-ml flow-through.

EXAMPLE 2

This example describes the purification of NO synthase.

Eighteen rat cerebella were homogenized in 100 ml of ice-cold buffer A [50 mM Tris-HCl, pH 7.4/1 mM EDTA/antipain (10 mg/liter)/leupeptin (10 mg/liter)/soybean trypsin inhibitor (10 mg/liter)/pepstatin (10 mg/liter)/chymostatin (10 mg/liter)/phenylmethylsulfonyl fluoride (100 mg/liter)], and all subsequent procedures were carried out at 4° C. The homogenate was centrifuged at 20,000×g for 15 min, and the supernatant was loaded at 2 ml/min onto a 20-ml column of diethylaminoethyl (DEAE) equilibrated with buffer A. The column was washed with 50 ml of buffer A and eluted with a 100-ml linear gradient of 0–400 mM NaCl in buffer A. Fractions (2.5 ml) were assayed for enzyme activity.

Fractions containing the first peak of activity from the DEAE column (see FIG. 1) were pooled and added to 2 ml of 2', 5'-ADP agarose equilibrated in buffer B (10 mM Tris-HCl, pH 7.4/1 mM EDTA/5 mM 2-mercaptoethanol). After a 10-min incubation, the suspension was poured into a fritted column, which was washed with 50 ml of buffer B with 0.5M NaCl and then with 20 ml of buffer B alone. NO synthase was eluted with 8 ml of buffer B containing 10 mM NADPH.

In our preliminary efforts to purify NO synthase, we observed that enzymatic activity adheres to a DEAE column and can be eluted by 1M NaCl. However, with gradient elution of NaCl, enzymatic activity was not recovered in eluate fractions, suggesting the separation during purification of the enzyme from an important cofactor. Since NO formation requires $Ca^{2+}$, we speculated that calmodulin might be involved. Addition of calmodulin to DEAE eluate fractions restores enzyme activity. NO synthase activity elutes in one sharp, major peak followed by a smaller peak of activity, which is observed reproducibly in multiple experiments.

For purification of NO synthase, we have focused on the first, major peak of enzyme activity eluting from the DEAE column, which provides a 5.6-fold purification of enzyme activity with 60% recovery (Table 1, FIG. 1). Further purification utilized affinity chromatography with a 2', 5'-ADP-linked agarose column. NO synthase activity adheres to this column and is not eluted by 0.5M NaCl. After the 0.5M NaCl wash, NO synthase activity can be eluted with 10 mM NADPH, providing a 1000-fold purification of enzyme activity in this step. The overall purification of NO synthase utilizing two steps, DEAE chromatography and 2',5'-ADP affinity chromatography, affords a 6000-fold purification of enzyme activity with 30% recovery. The purified enzyme eluting from the ADP affinity column appears homogeneous, constituting a single band on SDS/PAGE (FIG. 3). The molecular mass of this band is ≈150 kDa. To estimate the molecular mass of the native enzyme, we conducted gel filtration chromatography with a Superose-6 column. NO synthase activity of the purified enzyme emerges from the column as a single peak coincident with the peak of protein, with an apparent molecular mass of 200 kDA, similar to the elution of β-amylase whose molecular mass is 200 kDA. Thus, purified NO synthase appears to be a monomer.

TABLE 1

| | Purification of NO Synthase | | | |
|---|---|---|---|---|
| Fraction | Protein μg | Recovery % | Specific activity, nmol-mg$^{-1}$ min$^{-1}$ | Purification,-fold |
| 15,000 × g supernatant | 180,000 | 100 | 0.16 | 1 |
| DEAE eluate | 20,000 | 60 | 0.9 | 5.6 |
| 2',5'-ADP agarose eluate | 9.0 | 30 | 960 | 6000 |

Enzyme was purified and fractions were assayed as described. Data presented are from a typical purification, which was repeated five times with closely similar results.

EXAMPLE 3

This example shows the effects of varying concentrations of calcium, calmodulin and NADPH on NO synthase activity.

Figure 2A:
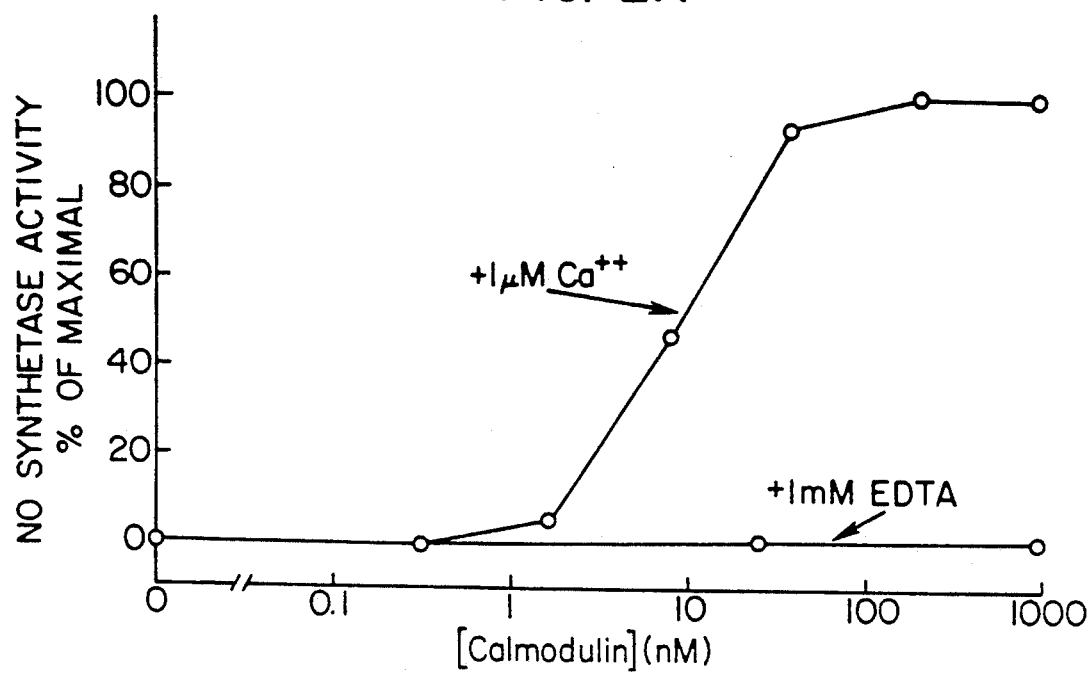
FIG. 2A shows the dependence of NO Synthase activity on calcium, as a function of calmodulin concentration.
Figure 2B:
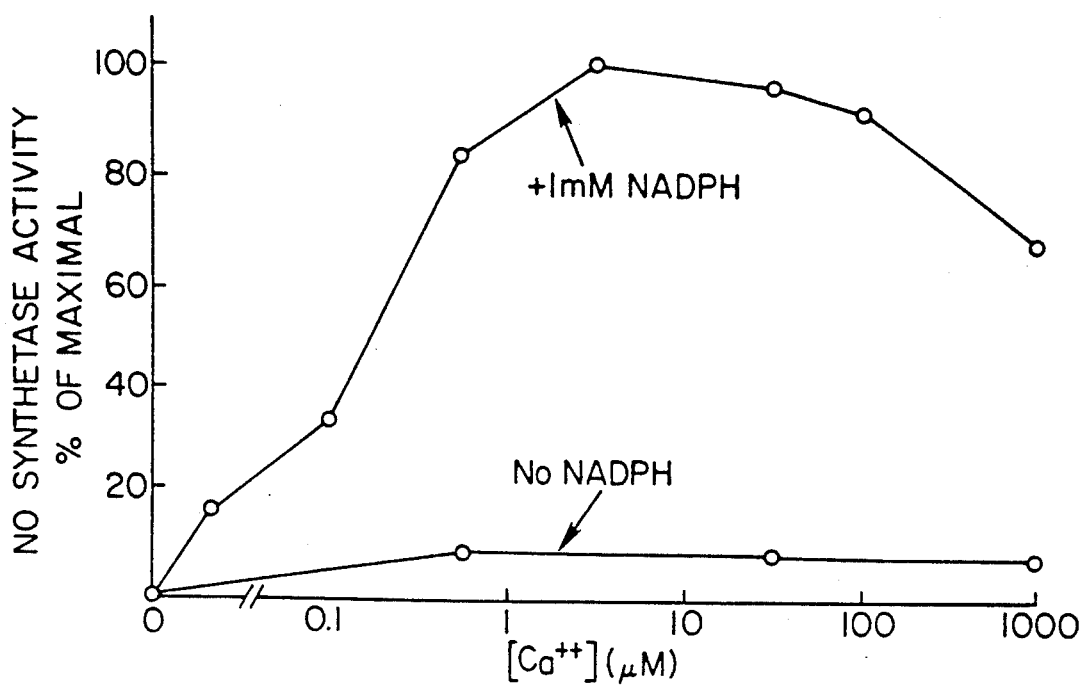
FIG. 2B shows the dependence of NO Synthase activity on NADPH as a function of calcium concentration.

Calmodulin is an extremely potent stimulator of NO synthase activity (FIG. 2A). In the presence of 1 μM $Ca^{2+}$, 50% of maximal stimulation of enzyme activity is apparent with ≈200 nM $Ca^{2+}$ with maximal enhancement of activity observed at 1 μM $Ca^{2+}$ and some reduction in activity at concentrations exceeding 100 μM $Ca^{2+}$. In the absence of NADPH, $Ca^{2+}$ fails to stimulate NO synthase activity.

EXAMPLE 4

This example demonstrates the effect of calmodulin antagonists on NO synthase activity.

In crude cerebellar supernatant preparations, calmodulin is not required to demonstrate enzyme activity and added calmodulin (1 μM) has no influence on enzyme activity. However, trifluoperazine, a calmodulin antagonist, inhibits enzyme activity of crude preparations with an $IC_{50}$ for trifluoperazine in crude supernatant preparations of vascular endothelial tissue, indicating that regulation of the endothelial and brain enzymes by calmodulin is similar. Trifluoperazine exerts multiple effects such as blockade of dopamine receptors. The drugs W-5 [N-6-aminohexyl)-1-naphthalenesulfonamide] and W-13 [N-4-aminobutyl)-5-chloro-2-naphthalenesulfonamide] are more selective calmodulin antagonists. In crude brain supernatant preparations, W-5 and W-13 inhibit NO synthase activity with respective $IC_{50}$ values of 50 and 25 μM.

EXAMPLE 5

This example demonstrates the properties of purified NO synthase.

The purified enzyme has high affinity for arginine with a $K_m$ of ≈2 μM, similar to what we observed previously in crude supernatant preparations. The $V_{max}$ of the purified enzyme is ≈1 μmol per mg of protein per min, similar to the $V_{max}$ values for other NADPH-requiring oxidative enzymes (Table 2). The $K_i$ for MeArg inhibition of NO synthase activity in the purified enzyme is ≈1.4 μM, similar to values we observed previously in crude preparations. The $EC_{50}$ for calmodulin enhancement of enzyme activity in the pure enzyme, 10 nM, is similar to the value observed in crude preparations. Also, the $EC_{50}$ for calcium stimulation of the purified enzyme is the same in the pure and crude preparations.

The purified enzyme is unstable. When stored at 0° C., 50% of the enzyme activity is lost in 2 hr, whereas the crude supernatant preparation loses 50% activity at 0° C. in 2 days. Stability is enhanced by storing the enzyme in bovine serum albumin (1 mg/ml)/20% (vol/vol) glycerol at −70° C. When stored in this way, the enzyme loses <50% activity in 7 days.

TABLE 2

| Properties of NO Synthase | |
|---|---|
| Arginine, $K_m$ | 1.5 μM |
| $V_{max}$ | 0.96 μmol per min per mg of protein |
| MeArg, $K_i$ | 1.4 μM |
| $Ca^{2+}$, $EC_{50}$ | 200 nM |
| Calmodulin, $EC_{50}$ | 10 nM |
| Calmodulin antagonists, | |
| $IC_{50}$ Trifluoperazine | 10 μM |
| W-5 | 25 μM |
| W-13 | 70 μM |

Purified enzyme was assayed as described. Values are means of two to six determinations, which varied by <20%.

EXAMPLE 6

This example demonstrates the production and use of antibodies which are immunospecific for calmodulin-dependent NO synthase.

Antibodies were raised in two rabbits and affinity purified with purified NOS. Antiserum was incubated with 50 mg purified antigen (immobilized in nitrocellulose after transfer from an SDS-polyacrylmide gel), eluted with 4M MgCl in 200 mM Tris-HCl (pH 7.4) buffer, and dialyzed against phosphate buffered saline with 0.1% TritonX100.

To ensure that the antiserum interacts with catalytically active NO synthase (NOS, EC1.14.23), we conducted immunoprecipitation experiments. The antiserum precipitates NOS activity in cerebellar homogenates, whether measured by the conversion of arginine to citrulline or by the formation of NO, with half-maximal precipitation at 10 $\mu g\ ml^{-1}$ antiserum IgG. In Western blot analysis the antiserum interacts with a single band of relative molecular mass 150,000 ($M_r$ 150K), the same as purified NOS. The density of the band varies amongst various brain regions and subdivisions of pituitary and adrenal glands in close parallel with the regional distribution of NOS catalytic activity. Antisera from two rabbits and affinity-purified NOS antibodies provide identical distributions by western blot analysis and by immunohistochemical staining. Immunoreactivity is absent with pre-immune serum or with serum preabsorbed with purified NOS.

EXAMPLE 7

This example demonstrates the molecular cloning of NO synthase coding sequences.

The nitric oxide (NO) synthase enzyme was purified to homogeneity as described in Example 1. The purified enzyme was run on an SDS gel and transferred to nitrocellulose. Trypsin was added to the nitrocellulose paper containing the enzyme in order to liberate peptide fragments. The peptide fragments were purified by reverse phase HPLC. The peptides were sequenced with an automated peptide sequencer. About 15 peptides were sequenced.

The above procedures were performed in order to obtain peptides whose sequence could be used as a basis for obtaining oligonucleotide probes for molecular cloning. In molecular cloning one frequently prepares a degenerate oligonucleotide based on the amino acid sequence of peptide fragments. For many proteins a mixture of degenerate oligonucleotide probes contains enough correct nucleotide sequence so that hybridization with the cDNA representing the protein to be cloned is possible. When such procedures were carried out for NO synthase, no appropriate clones could be identified. Accordingly, a new technique was developed in which a non-degenerate oligonucleotide probe was generated by polymerase chain reaction (PCR). This was done by taking two of the longest peptides, of 18 and 17 amino acids, and constructing degenerate oligonucleotide primers of 21 nucleotides based on the 7 amino acids at the carboxyl and amino termini of each of the two peptides. These oligonucleotides were employed in a PCR reaction to construct two non-degenerate oligonucleotide primers.

These two non-degenerate oligonucleotide primers were employed in a further PCR reaction to obtain a large polynucleotide probe. There was no way of knowing a priori whether one would obtain an appropriate probe, as the two oligonucleotide primers employed might have been located too far apart in the sequence of the NO synthase to permit amplification. Fortunately, we were able to obtain a 600 base pair amplified product for use as a polynucleotide probe to screen molecular clones.

The 600 bp polynucleotide probe was random prime labeled with $^{32}P$-ATP and used to screen a commercially obtained rat brain cDNA library from Stratagene. Eight overlapping independent clones were isolated and sequenced by double-stranded dideoxy sequencing. This procedure revealed a 4 kb open reading frame coding for a protein of about 150 kD, which corresponds to the molecular weight of NO synthase which we had previously purified.

The deduced amino acid sequence has been examined by computer program for homology with other known families of proteins. No major homology has been observed. A flavin binding site consensus sequence has been observed.

---

We claim:

1. A cDNA molecule which encodes all or a portion of a mammalian, calmodulin-dependent Nitric Oxide Synthase (NOS), said molecule comprising between about 12 nucleotides and 4,000 nucleotides.

2. The cDNA molecule of claim 1 which is labeled with a detectable moiety.

3. The cDNA molecule of claim 1 which encodes all of NO Synthase.

4. The cDNA molecule of claim 1 which has the nucleotide sequence shown in SEQ ID NO: 1.

5. The cDNA molecule of claim 1 which encodes the amino acid sequence shown in SEQ ID NO: 2.

6. The cDNA molecule of claim 1 which hybridizes to a molecule having the nucleotide sequence shown in SEQ ID NO: 1.

7. A cDNA molecule which encodes all or a portion of a calmodulin-dependent NOS, and hybridizes to a molecule having the nucleotide sequence shown in SEQ ID NO: 1, said molecule comprising between about 12 nucleotides and 4,000 nucleotides.

8. A recombinant host cell comprising the cDNA molecule of claim 1.

9. The recombinant host cell of claim 8 wherein said cDNA molecule encodes all of the Nitric Oxide Synthase.

10. The recombinant host cell of claim 8 wherein said cDNA molecule has the nucleotide sequence shown in SEQ ID NO: 1.

11. The recombinant host cell of claim 8 wherein said cDNA molecule hybridizes to a molecule having the nucleotide sequence shown in SEQ ID NO: 1.

* * * * *